United States Patent [19]
Jacobson

[11] Patent Number: 5,665,095
[45] Date of Patent: Sep. 9, 1997

[54] STEREOTACTIC GUIDANCE DEVICE

[76] Inventor: Robert E. Jacobson, 5995 SW. 71st., Third Fl., So. Miami, Fla. 33143

[21] Appl. No.: 356,517

[22] Filed: Dec. 15, 1994

[51] Int. Cl.⁶ .................................................. A61B 19/00
[52] U.S. Cl. ........................ 606/130; 604/116; 128/653.1
[58] Field of Search ........................... 606/130; 604/116; 128/653.1

[56] References Cited

U.S. PATENT DOCUMENTS

| | | | |
|---|---|---|---|
| 4,350,159 | 9/1982 | Gouda | 606/130 |
| 4,463,758 | 8/1984 | Patil et al. | 606/130 |
| 4,571,243 | 2/1986 | Froning et al. | 606/130 |
| 4,653,509 | 3/1987 | Oloff et al. | 606/130 |
| 4,706,665 | 11/1987 | Gouda | 606/130 |
| 4,791,934 | 12/1988 | Brunnett | |
| 4,875,478 | 10/1989 | Chen | 606/130 |
| 5,030,223 | 7/1991 | Anderson et al. | 606/130 |
| 5,047,036 | 9/1991 | Koutrouvelis | |
| 5,280,427 | 1/1994 | Magnusson et al. | 606/130 |
| 5,281,232 | 1/1994 | Hamilton et al. | 606/130 |
| 5,308,352 | 5/1994 | Koutrouvelis | |
| 5,383,454 | 1/1995 | Bucholz | 606/130 |

Primary Examiner—Robert A. Hafer
Assistant Examiner—Benjamin K. Koo
Attorney, Agent, or Firm—McHale & Slavin, P.A.

[57] ABSTRACT

A portable stereotactic guidance having coordinated targeting and delivery assemblies. Aligning and orientating a medical instrument in a three-dimensional plane by specific cartesian coordinates or live imaging. The device may operate in conjunction with an X-Ray or CT scanner so as to image a patient allowing the surgeon to accurately introduce a probe such as a needle, cannula, or guide wires into the human body at a preselected angle. The device fits over a patient using and is used in conjunction with an alignment guide to read X, Y and Z coordinates as well as associated angles for precise orientating of a delivery system. Provision is made for aligning of the device can be performed during real time X-Ray or scanning through a target assembly having cross hatching to target an object for use as a reference point. Once a target is set, the delivery system is aligned by sliding the delivery system within a cartesian coordinate system thereby rotating the stir ups along a polar coordinate system. The delivery system can be aligned by rotation of the stir ups to either specified angels or desired images. The delivery system can be used independently from the targeting system.

24 Claims, 5 Drawing Sheets

STEREOTACTIC GUIDANCE DEVICE

FIELD OF THE INVENTION

This invention relates to stereotactic devices and more particularly to a guidance device capable of precision orientation of surgical devices in a three-dimensional plane.

BACKGROUND OF THE INVENTION

Guidance devices are well known in the art for use with X-ray or scanning devices providing a surgeon with multi-dimensional viewing of the skeletal and supporting structure wherein various medical procedures on the body can be performed. Such devices provide a stability to a surgical instrument not possible by human hands and in many instances allow hands free operation. Typically the guidance device is set upon a structure used in combination with a scan table. The structure can be moved yet maintain a level position despite vertical or horizontal disposition. Bracketry is available to support items such as a needle. A protractor may be used to determine the desired plane, the rotation of which is set to match angulation of a target path as determined by a scan.

The CT scan allows the determination of the ultimate target path so as to avoid penetration of vital structures such as nerves or vessels thereby minimizing both the time of surgery and the extent thereof. Common to prior art devices is their targeting limitations.

Prior art discloses a number of stereotactic devices which are dependent upon the diagnostic mapping of a patient such as those generated by a multi-plane scanner for use in locating an internal region of interest in advance of a clinical procedure.

Variations of stereotactic devices include a means for rotating a probe holder in a vertical or horizontal plane using protractors to verify finite movement in length or angle. The aiming of the probe is accomplished by use of a CT scan providing coordinates of a presumed target within the body. A scan can be made and the aim of the medical device verified by superimposing the target on a scanner printout. When a guide is accurately aimed both in the coronal and sagittal planes, a medical instrument can be inserted into the body at the proper depth, the position verified by a CT scan or roentgenogram.

Stereotactic devices are unique in that they are adaptable to align and orientate a variety of medical instruments such as guide wires, needles, and cannulas into the human body so as to perform such procedures as percutaneous dissectomies, cysts, aspirations, tumor localizations, biopsies and the like type operations.

U.S. Pat. No. 4,791,934 discloses a clinical method in positioning a surgical instrument by first imaging a patient so as to produce a three-dimensional diagnostic mapping data, transferring the patient to a treatment station by generating a dimensional calibration reference image through the patient followed by configuring an analogous two-dimensional image from the three-dimensional diagnostic mapping data. The calibration reference and diagnostic data of the images are then determined to place the relative orientation between the patient and the three-dimensional mapping data so as to orient the surgical instrument in a precise position relative to the patient for treatment of the structure.

U.S. Pat. No. 5,308,352 discloses a stereotactic device which is adapted for use with a scanner when a patient is placed upon the surface of a CT scan table. The device consists of a carrier for a medical device which is placed on a horizontal bridge supported by two vertical legs that are slidably adjustable along the horizontal length of the scan table with a means for locking thereto. The limitation to the instant invention is most notable on the rotation of the carrier mechanism relative to the vertical legs. The radial rotation of the medical device is limited in its holding of the device that would be inserted into the body due to the fixed position of the vertical legs. With such technology the surgeon can accurately place biopsy needles in drainage catheters within a body carefully avoiding critical areas such as nerves, veins, and muscle that may adversely affect the patient.

U.S. Pat. No. 5,047,036 discloses a stereotactic guidance device consisting of a stainless steel bridge which spans a scanner table and is either mounted directly to the table or mounted on two anchored vertical side rails permanently mounted to the floor.

Thus, what is needed in the art is a portable, true stereotactic guiding mechanism for medical devices may work in conjunction with an X-ray or CT scanner so as to accurately position a surgical instrument in a three-dimensional plane so as to allow a surgical operation on a patient with minimal setup time or exploratory disruption to the body.

SUMMARY OF THE INVENTION

The instant invention operates to provide a surgeon with a portable stereotactic guidance device for precisely orientating medical devices such as needles, cannulas and guide wires. The device consists of a portable support structure which is placed upon a CT scanning or X-ray table either before or after the placement of a patient. Vertical legs are disposed on each side of the patient and a cross connect forming a base support structure maintains the legs in a stationary position. Along a top surface of the support structure is an interface frame assembly which can move along the longitudinal length of the base structure. A guide track with matching alignment slats having precise tolerances is operatively associated with each support structure to eliminate lateral movement. A handwheel provides precision adjustment of the interface frame assembly along the longitudinal length of the base support structure.

A arch frame assembly is placed within the interface frame assembly and operates to move along the width of said interface frame assembly. The interface frame assembly includes a guide track with matching alignment slats attached to the arch frame assembly, which allows movement of the arch frame from side to side within the confines of the interface frame assembly. A hand wheel provides adjustment in its movement along the width of the interface frame assembly. The arch frame assembly operates to hold an upright structure capable of articulating approximately 45 degrees in a forward and reverse position and operates to secure a transparent holding bracket that tilts from left to right. The holding bracket rotates along a pivot point approximately thirty degrees from a normally perpendicular stance.

An alignment target frame assembly is incorporated into the aforementioned structure formed from two vertical legs having a cross connect external the base structure and extending slightly above the surface of the movable support structures. Along one vertical leg of the target frame assembly is a sight hole having a circular viewing port with cross hatches that allow the surgeon to scan through the port and line up the device with a portion of the patient's body. An angle can be determined in relation to the longitudinal support structure by reference to a guide wire connected between the viewing and secondary support structure wherein the angle can be read on a protractor face disposed about the surface of the port. The vertical side rails are movable along the length of the primary support structure by use of a hand wheel providing precision movements so as to permit repositioning of the device upon angular adjustment.

In operation, a scan of a patient can be made wherein the device can be set according to the patient's body. All measurements are taken in a three-dimensional format so as to allow the surgeon to repeat placement of the alignment device when the actual surgery is to be performed. The device can be adjusted to the previously aligned patient's body position wherein each support structure is adjusted to the previously depicted measurement location so as to set forth a probe holder in the exact position as previously planned so as to lessen surgery time. The surgeon may begin an operation and verify the process by real time scanning.

Once a target is set, the delivery system is aligned by sliding the delivery system within a cartesian coordinate system thereby rotating the stirrups along a polar coordinate system. The delivery system can be aligned by rotation of the stirrups to either specified angels or desired images. The delivery system can be used independently from the targeting system. For example the placement of a pedicle screw may be performed by set angle ∝ at 10 degrees, vary angle ø to match measured angle of vertebrae from X-ray, then sliding interface frame and arch frame to a desired position.

Thus, an objective of the invention is to provide a stereotactic guidance device capable of three-dimensional plane adjustment.

Still another objective of the invention is to teach a method of targeting and delivery of surgical devices that can be used with computer guided equipment such as robotic arms.

Another objective of the instant invention is to provide a portable guidance device that allows a surgeon to place a surgical instrument in a secure hands free position.

Still another objective of the instant invention is to provide a stereotactic guidance device that operates in a real time mode with an X-ray or scanner.

Yet another objective of the instant invention is to provide a separate alignment target frame assembly which operates in conjunction with one of the support structures so as to provide a cross-sectional displacement of the apparatus in combination with an angular disposition a primary carrier structure.

Still another objective of the instant invention is provide a stereotactic targeting and delivery systems that can be used with other wands, frameless, stereotactic arc's such as robotic arms.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objectives and features thereof.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1:
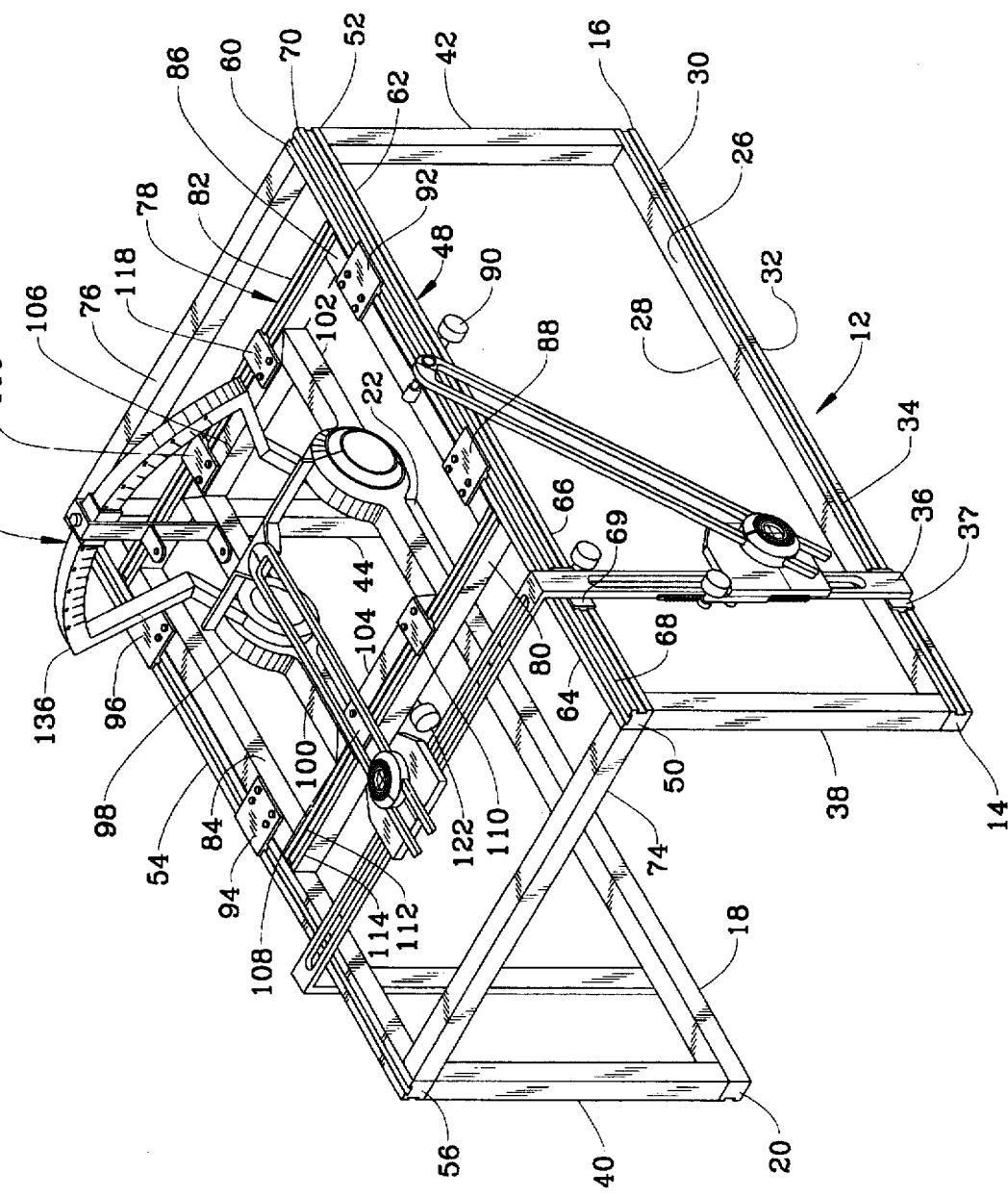
FIG. 1 is a perspective view of the instant invention numerically depicting the primary and longitudinal support structure.
Figure 2:
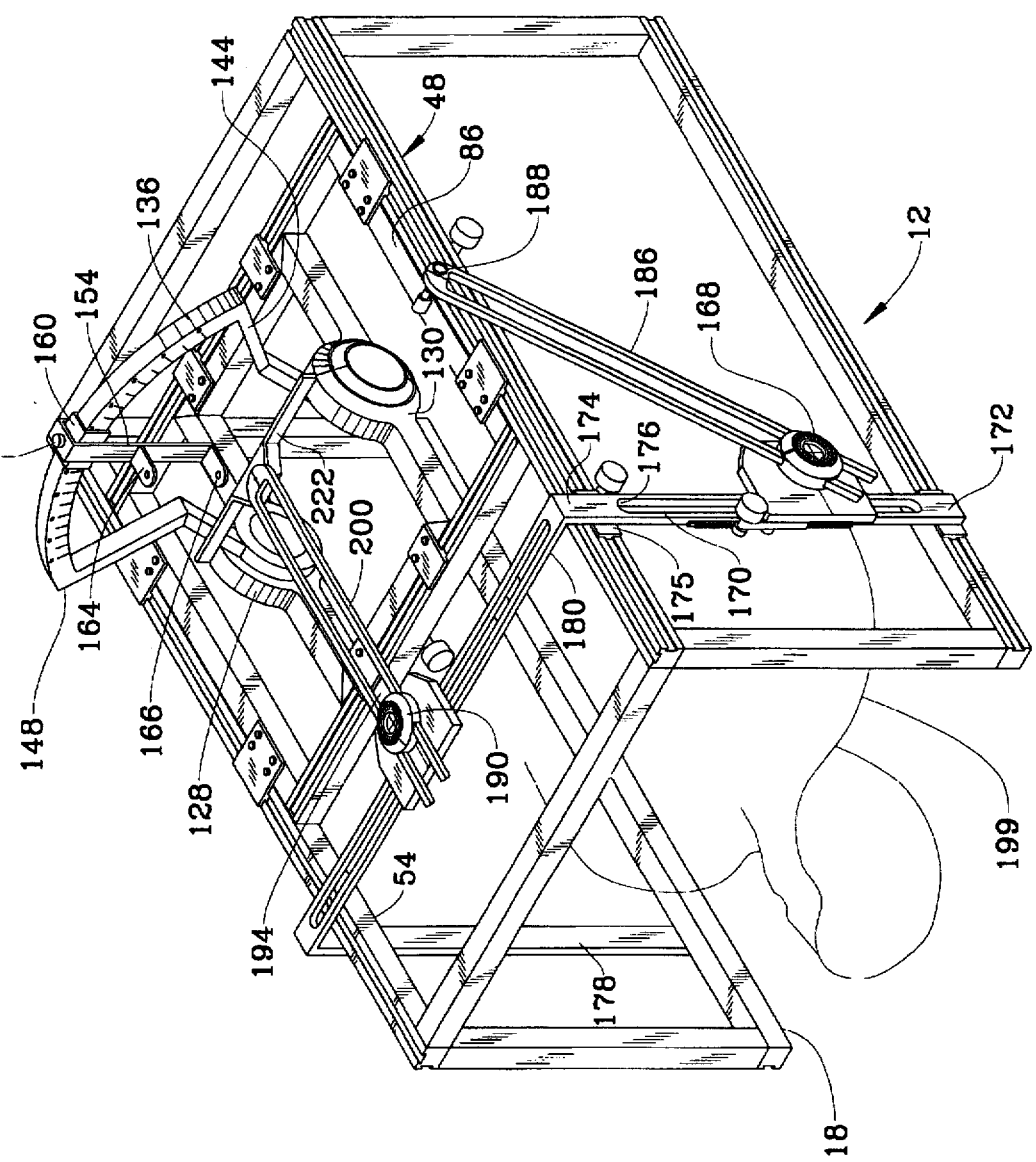
FIG. 2 is a duplicate of FIG. 1 with numerical depiction of the secondary support members and alignment mechanisms and providing a pictorial of a patient within the structure.

Now referring in general to FIGS. 1 and 2, shown is the instant invention with a first lower support rail 12 having a longitudinal length from a first end 14 to a second end 16. The lower support rail 12 is parallel and spaced apart a predetermined distance in correlation to a conventional CT or X-ray scanning table to a second lower support rail 18 having a first end 20 and second end 22. The lower support rails include pegs or peg holes along the bottom thereof, not shown, for securing to a support table. Lower support rail 12 is further defined as having an upper surface 26, inner surface 28, outer surface 30, and a lower surface 32. The support rail 12 has a dove tail cavity 34 along the outer surface 30 of the longitudinal length of the rail which operates as a guide track. As will be described later in this specification, the dove tail cavity 34 operates to position a vertical alignment target frame assembly 36 in a parallel and perpendicular position with the structure as further defined later in this specification. The dove tail cavity may be replaced by any type of support surface without defeating the intent of this invention. An alignment slat 37 fits within the guide track for precision movement. The second lower support rail 18 is a mirror image of the first support rail 12 and has the same support surface.

The delivery system is raised over the body of a patient a predetermined distance by four corner legs. Leg 38 is positioned over end 14 in a parallel planar position with a upstanding leg 40 positioned over the end 20 of the second lower support rail. Rear support is provided by leg 42 located at second end 16 of the lower support rail 12 and leg 44 positioned at the second end 22 of the lower support rail 18. An upper structure is used to support the delivery system and is defined by a first upper support rail 48 having a longitudinal length defined by a first end 50 and a second end 52. A second upper support rail 54 having a first end 56 and a second end 58, each upper support rail forming a mirror image thereof. The first upper support rail is further defined by an upper surface 60, lower surface 62, inner surface 64 and outer surface 66. Guide track 68 is disposed along the longitudinal length of the rail and operatively associated with an alignment slat 69 coupled to the vertical target frame assembly 36, the guide track maintains said target frame assembly 36 in perpendicular correlation between the upper and lower rails on each side of the device. It should be noted that any guide track shape or mechanism which maintains the target frame assembly 36 in a perpendicular manner with the upper and lower support rails is deemed within the scope of the invention.

The upper support rails are coupled together along the first end 50 and 56 by cross support member 74 with cross support member 76 placed between second ends 52 and 58 providing rear support. The operation of the target frame assembly will be explained later in this specification as it operates with a moveable structure that has not been described.

Within the upper support rails 48 and 54 is positioned a interface frame assembly 78 defined as a substantially rectangular support having a first end 80 and a second end 82 and two parallel disposed side supports 84 and 86 each having a longitudinal length less than the longitudinal length of the first and second upper support rails 48 and 54. The support structure 78 includes alignment slats for precision movement along the length of said upper support rails as shown by engagement brackets 88 and 92 secured to one side of the slidable support structure 78 as are brackets 94 and 96 to the opposite side, each of which operates with the dove tail type cavities 70 disposed within each said upper support rail. Positioned along the first upper support rail 48 is a means for moving the interface frame such as adjustment knob 90 coupled to support rail 86 wherein rotation of the knob 90 allows precise movement of support structure along the length of said upper support rails. Knob 90 can be coupled to a precision cut threaded rod, not shown, disposed beneath or within the upper support rail allowing the forward or reverse movement of the support structure 78. The engagement mechanism is preferably coated with a non-stick surface such as teflon so as to eliminate friction during movement of the structure 78.

Arch frame assembly 98 is disposed within the interface frame 78 and is defined a side rail 100 which is coupled to a second side rail 102 by first end cross connect 104 and second end cross connect 106. The rails and cross connects form a rigid support platform which is slidable along the width of the interface frame 78 along end members 80 and 82, in a similar fashion as the interface frame 78 moves along the upper support. End cross connect 104 includes a first and second bracket 108 and 110 having a means for inserting into a guide track 112 formed along an upper surface 114 of end cross connect 80. Similarly, brackets 116 and 118 are operatively associated with an upper surface of end cross support 82 each having alignment slats operatively associated with the tracks. The arch frame assembly 98 includes an adjustment mechanism 122 which engages the interface frame allowing the operator to precisely move the arch frame assembly 98 along the width of the interface frame assembly 78.

Figure 6:
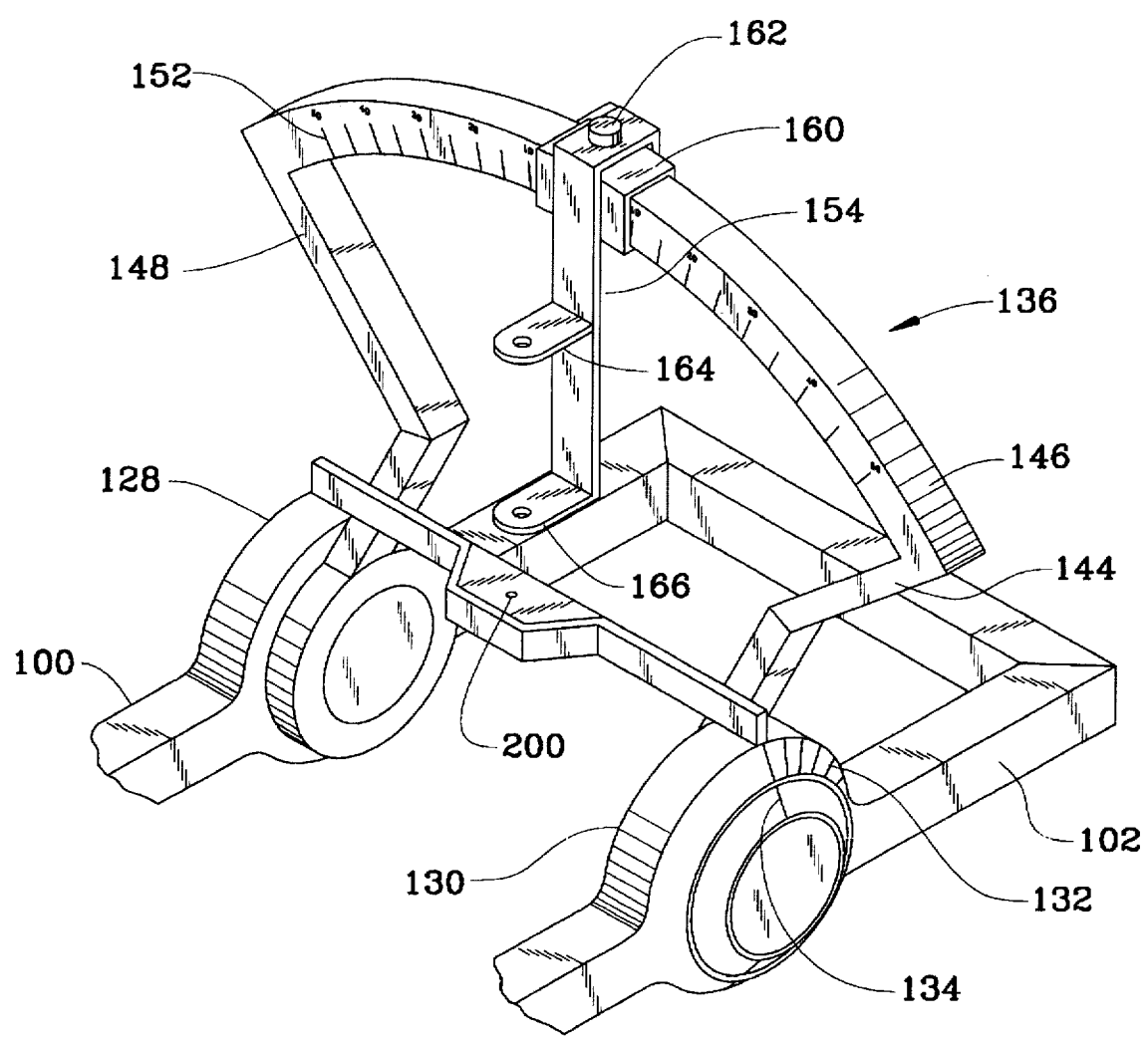
FIG. 6 is a perspective view of the upright support member.

As further illustrated by FIG. 6, side rails 100 and 102 includes a circular shaped support bracket 128 and 130 for receipt of an arch frame defined by an arc 136 having a lower member 144 which is pivotally coupled to the support bracket 130 by use of removable tab inserts, not shown. The removable tab inserts allow the operator to insert a variety of delivery frame assemblies from various manufacturers into the arch frame assembly. For instance, a surgeon who is familiar with the delivery frame assembly used with head surgery would be more receptive to using that delivery system which can be positioned within the arch frame. The circular shaped support brackets allow rotation of the arc 136 allowing the angle of rotation to be read along frame marking indicia 132 and alignment pointer 134. The lower members 144 and 148 lead to an angularly shaped inverted curved measurement bar 146. The measurement support 146 further sets forth adjustment angle positioning by viewing of the measurement indicia 152 providing exacting positioning of the delivery assembly 154. The delivery assembly 154 is defined as a substantially flat bar constructed of a transparent material coupled to the arc 136 by sleeve 160 and locking mechanism 162. The delivery assembly 154 can be removed without changing of the arch. A typical delivery assembly will include holding bracket's 164 and 166 for coupling syringes, cannulas, guide wires and the like medical devices.

As described in detail later in the specification, an attachment point 200 is provide for engaging of an alignment wire for position of the arc 136. The attachment point 200 is secured to each side surface of the frame assembly 100 and 102, preferably along a portion of the circular support so as to raise the attachment point over the surface of the device for proper clearance.

When the device is placed over a patient 199 as depicted in FIG. 2, the delivery system is positionable by movement of the arc 136 in a forward or backward direction viewable along rotational brackets 128 and 130. The delivery system 154 can be moved from side to side and the arch frame assembly 98 positioned along a longitudinal length of the device by movement of interface frame assembly 78.

Figure 3:
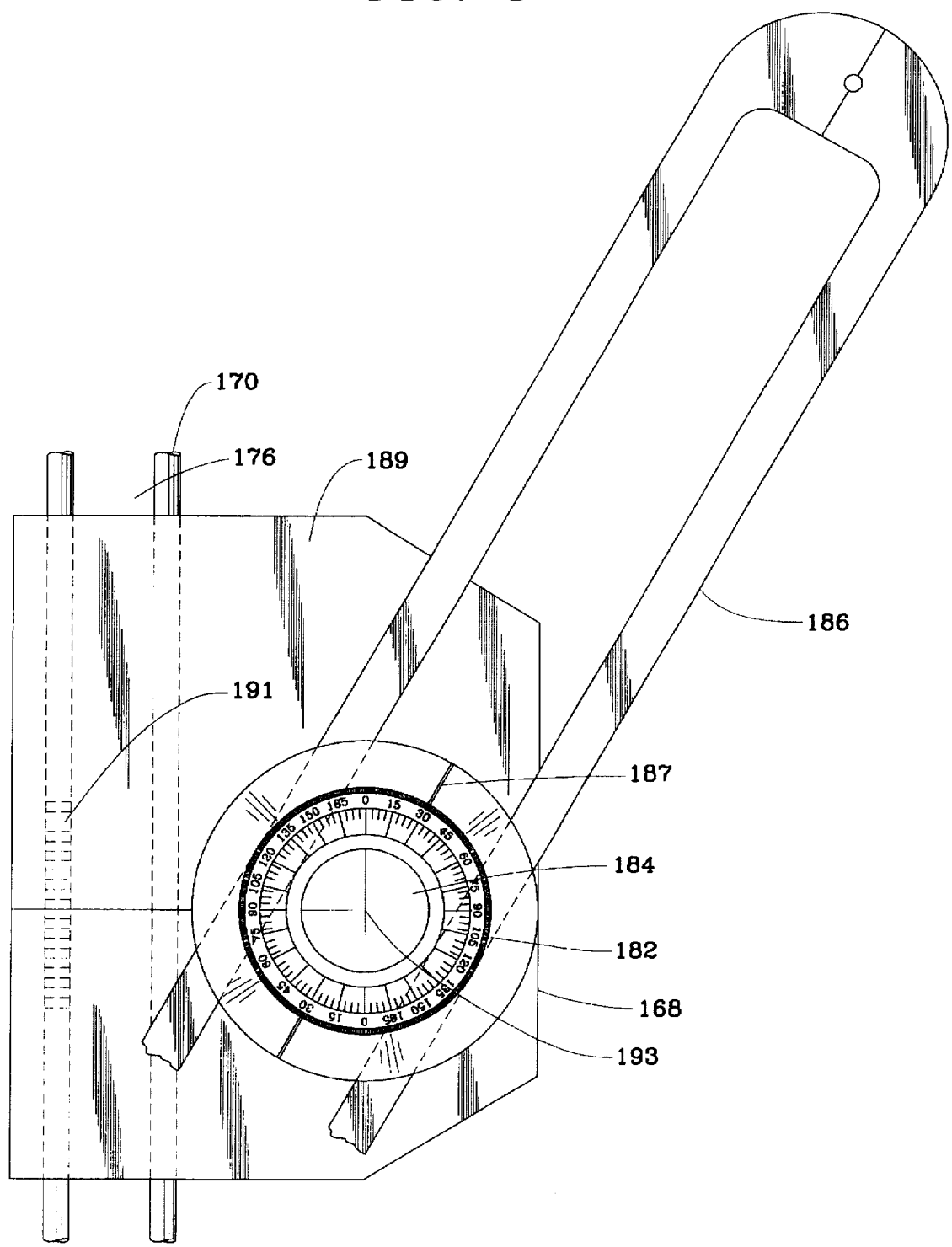
FIG. 3 is a plane view an alignment guide having a positioning protractor.

Target frame assembly 36 is a unique alignment device that provides infinite repeatability by use of two identical target assemblies defined as sighting tubes 168 and 190. The first upright leg 170 of the target frame assembly 36 has a lower end 172 operatively associated with the lower support rail 12 and having a longitudinal length extending a second end 174 above the surface of the upper support rail 48. A portion 175 of said upright 170 includes a means for attaching to a side surface of said upper support rail 48 wherein movement of said leg 170 is maintained in a perpendicular format to said upper and lower support rails. Along the length of said upright leg 170 is a slot 176 formed along a section thereof for placement of said target assembly 168. Similarly, leg 178 is secured to lower support rail 18 and upper support rail 54 wherein movement of either upright is uniform by cross member 180. The target assembly 168 includes a protractor 182 disposed around a through hole 184 that operates to set forth an angle when used in conjunction with stirrup 186. A free end of said stirrup 186 is coupled to the slidable support structure 78 by side stirrup connector 188 which extends above the surface of said first upper side rail 48 and secured to the upper surface 86 of said slidable support structure 78. In operation if the slidable support structure 78 is slid along the longitudinal length of the device, as further illustrated in FIG. 3, the stirrup 186 changes angles and the angle can be read by protractor surface 182 along alignment marker 187. The vertical position of the target assembly 168 can be moved wherein the height can be recorded through a transparent support housing 189 having markings 191 on the upright. The target assembly 168 includes throughhole 184 having internally disposed cross hair hatching 193, shown in FIG. 3 wherein a real time X-ray therethrough would allow the surgeon to align the device to an internal body structure. Once the device is placed over a patient, a scan or X-ray of the body can be performed through the cross hatching 193 of the target assembly 168 wherein positioning thereof can be read by the protractor 182. Similarly, the slidable support structure 78 can be located over a portion of the body to be operated upon for direct placement of the delivery system.

Figure 4:
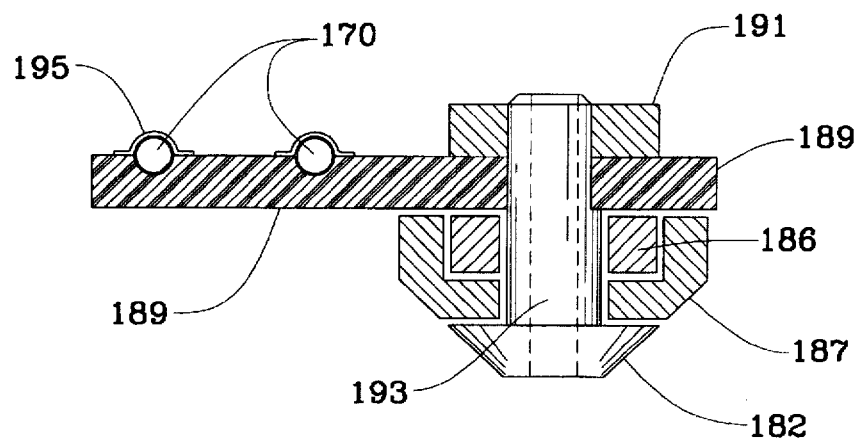
FIG. 4 is a cross sectional side view of the positioning protractor of FIG. 3.
Figure 5:
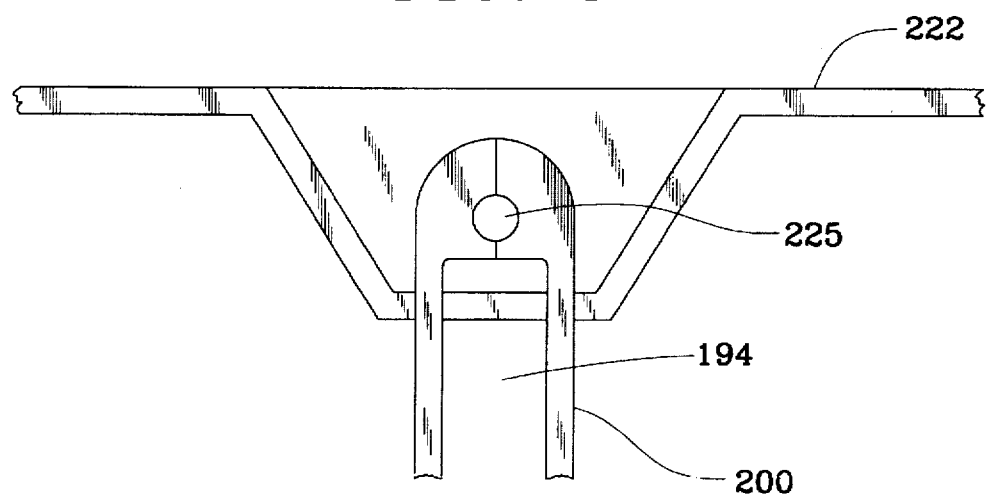
FIG. 5 is a top plane view of the horizontal alignment guide attachment to the upright support member.
Figure 5A:
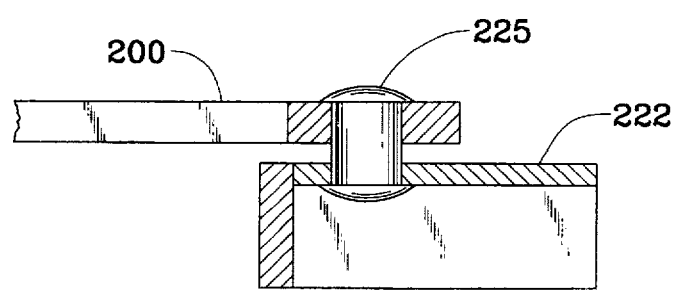
FIG. 5A is a side view of FIG. 5.

Upper alignment guide 190 is positioned along the horizontal cross brace 180 having stirrup 200 providing a direct correlation to the arc 136 by cross member 222 as further shown in FIGS. 5 and 5A. The alignment guide 190 can be slid along the cross brace through slot 194 in correlation with the movement of arch frame assembly 98. The protractor guide and target assembly used on the vertical alignment guide and horizontal target frame assembly alignment guide are identical and thus only the vertical guide is described by separate illustration. Thus, each guide consists of a protractor 182 having numerical indicia positioned along a surface of the protractor. The stirrup 186 is coupled to stirrup coupler 188 which is slidably securable to the target assembly by placement within the alignment marker 187 which further operates as a spacer, see FIG. 4. The stirrup 186 is held in position by lock nut 191 as the protractor 182 is placed on the end of a securement bolt 193. The transparent support housing 189 is slidably secured to the upright leg 170 by coupling brackets 195.

Movement of the interface frame translates to movement of the stirrup 186 which slides along the length of the target assembly 168. As the stirrup is positioned in an offset position, the indicia is read along surface 182 with parallel alignment marker 187. Shown in the illustration is the stirrup at a thirty degree angle. The guidelines are disposed around the outer surface of the protractor providing ease of alignment and verification of angles. In the middle of the target assembly 168 is shown the cross-hairs 193 used with an active X-ray or radio X-ray allowing the surgeon to precisely point the alignment guide to a portion of the patient's body providing a baseline or alignment point from which all adjustments can be ascertained.

It should be noted that the alignment wire protractor surface and adjustment slot depicted in the vertical alignment guide is identical to the horizontal alignment guide except for the point of attachment. In the vertical alignment guide, stirrup 186 is rotatably coupled to side stirrup connector 188. The horizontal alignment guide 190 uses stirrup 200 with a point of attachment 225 by a pinion guide inserted into cross member 222.

While what has been described is a mechanical system, it will be obvious to one skilled in the art that the teaching herein is of a method of targeting and delivery of surgical devices. Use of this teaching will allow one skilled in the art to incorporate the teachings into various embodiments including computer software programming for robotic delivery. In accordance with this teaching, the method of targeting and delivery can be followed from the steps of: positioning a base support frame over the body of a patient placed upon a support table; inserting an interface frame onto said system frame; placing an arch assembly onto said interface frame; coupling a targeting frame assembly to said system frame with stirrups coordinating said targeting frame to said interface frame and said arch assembly; attaching a delivery bracket to said arch frame assembly; means for aligning said delivery bracket to a predetermined position by setting an angle of lateral and longitudinal entry.

The means for aligning includes the steps of: sliding said target frame along said base system frame to a desired location and locking in position so as to set the X coordinate; sliding said side mounted target assembly along said target frame to a desired location and locking said side target assembly in position providing coordinate Y; and sliding said top target assembly along said target frame to a desired location and locking in position for providing a coordinate Z.

The method of setting an angle of lateral entry comprises the steps of: sliding said interface along said base system frame until side stirrup aligns with a desired angle wherein said slide interface frame is locked in position; and adjusting a desired angle of the arch rotator with arch frame to match angle side stirrup and lock in position.

The method of setting an angle of longitudinal entry comprises the steps of: sliding said arch frame along said interface frame until said top stirrup aligns with a desired angle wherein said arch frame is locked in position; and sliding said delivery system along said arch assembly to match angle of said top stirrup wherein said delivery system is locked into position.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A surgery guidance device comprising:

a base for securing to a table, said base forming an adjustable guidance carrier for positioning over a patient's body characterized by two horizontally disposed spaced apart rigid lower support members each having a length with a first end and a second end, said lower support members having upwardly facing support legs positioned perpendicular thereto coupling horizontally disposed spaced apart rigid upper support members placed in a parallel plane to said lower support members, each upper support member having a length with a first end and a second end attached to said support legs, each upper and lower support member as joined by said support legs forming a side member assembly, and each end of each upper support member having a cross brace member disposed therebetween;

an interface frame assembly slidably disposed within said upper support members, said frame having an upper surface and a width and a length less than a length of said base, said upper surface of said interface frame assembly including at least one side rail crossing said width of said interface frame assembly, each said side rail having a guide track on its upper surface;

an arch frame assembly slidably disposed within said interface frame assembly having a width and a length, said arch frame assembly width less than said width of said interface frame assembly; an alignment slat secured to said arch frame assembly with said guide track operatively associated with said alignment slat; an arc member pivotally coupled to said arch frame assembly; means for tilting said arc member; and a delivery system pivotally coupled to said arc member.

2. The guidance device according to claim 1 wherein an upper surface of each said upper support member includes a guide track disposed between said first end and said second end operatively associated with an alignment slat secured to said interface frame assembly.

3. The guidance device according to claim 1 including a means for moving said interface frame assembly along said length of said upper support members.

4. The guidance device according to claim 1 wherein said interface frame assembly includes a position determining means in relation to said base support.

5. The guidance device according to claim 1 including a means for moving said arch frame assembly along said width of said interface frame assembly.

6. The guidance device according to claim 1 wherein said arch frame assembly includes measurement indicia for positioning in relation to said interface frame assembly.

7. The guidance device according to claim 1 wherein said arch frame assembly includes a circular shaped receptacle along each side support rail for rotatable receipt of said arc member, said receptacle having measurement indicia placed along a side surface to assist in angular positioning of said arc member.

8. The guidance device according to claim 7 wherein said receptacle includes a means for securing said arc member in a fixed position.

9. The guidance device according to claim 1 including an alignment target frame assembly defined by two vertically disposed legs slidable along the longitudinal length of each said side member assembly and connected by a horizontally disposed cross connect set a predetermined distance above said base support member.

10. The guidance device according to claim 9 wherein said alignment target frame assembly includes at least one targeting device having a means for real time positioning and a means for determination of angular positioning to said interface frame.

11. The guidance device according to claim 10 wherein said means for real time positioning is further defined as a sight tube having cross-hairs for imaging therethrough.

12. The guidance device according to claim 10 wherein determination of angular positioning is performed by reading of angular degree indicia positioned along the circumference of a securement bolt having an alignment marker maintained in a parallel position to a stirrup wire coupled to said interface frame.

13. The guidance device according to claim 10 wherein said means for real time positioning is further defined as a sight tube having cross-hairs for imaging therethrough.

14. The guidance device according to claim 10 wherein determination of angular positioning is performed by reading of angular degree indicia positioned along the circumference of a securement bolt having an alignment marker maintained in a parallel position to a stirrup wire coupled to said arch frame assembly.

15. The guidance device according to claim 1 wherein said delivery system is constructed from transparent material with at least one bracket available for releasably coupling a surgical tool.

16. The guidance device according to claim 1 wherein including a means for locking said delivery system to said arc member having positioning indicia disposed on said arc member.

17. A surgery guidance device for use in combination with a X-Ray or CT scanner comprising:

a base defined by two horizontally disposed spaced apart rigid lower support members each having a length with a first end and a second end with upwardly facing support legs positioned perpendicular thereto coupling horizontally disposed spaced apart rigid upper support members placed in a parallel plane to said lower support member, each upper support member having a length with a first end and a second And attached to said support legs, and each end of each upper support member having a cross brace member disposed therebetween;

a interface frame assembly slidably disposed within said upper support members, said interface frame having a width and a length less than a length of said base support member;

a means for moving said interface frame assembly along a length of said base;

an arch frame assembly slidably disposed within said interface frame assembly having a width and a length, said arch frame assembly width less than said width of said interface frame assembly;

a means for moving said arch frame assembly along a width of said interface frame;

an arc member coupled to said arch frame assembly defined as a substantially inverted U-shaped housing pivotable along said width of said arch frame assembly;

means for tilting said arc member, said means for tilting including a means for securing said arc member in an angular position;

a delivery system pivotally coupled to said arch member;

an alignment target frame assembly defined by at least one vertically disposed leg slidable along the longitudinal length of one said side member coupled to said interface frame assembly; and a means for securing said base to an X-Ray or scanning table.

18. The guidance device according to claim 17 wherein said alignment target frame assembly includes a positioning bracket slidable along a vertical length of said first leg.

19. The guidance device according to claim 18 wherein said positioning bracket includes a through hole having a centrally disposed positioning marker and exterior angular indicia marking.

20. The guidance device according to claim 17 wherein said side member is coupled to said interface frame assembly by a rigid rod having a first end rotatably coupled to a positioning bracket and a free end slidably attached to said interface frame assembly, said rigid rod angular displacement read against exterior angular indicia marking.

21. A method of targeting and delivery of surgical devices said method comprising:

positioning a base support frame over the body of a patient placed upon a support table;

inserting an interface frame onto said system frame;

placing an arch assembly onto said interface frame;

coupling a targeting frame assembly to said system frame with stirrups coordinating said targeting frame to said interface frame and said arch assembly;

attaching a delivery bracket to said arch frame assembly;

means for aligning said delivery bracket to a predetermined position by setting an angle of lateral and longitudinal entry.

22. The method of targeting according to claim 21 wherein said means for aligning includes the steps of:

sliding said target frame along said base system frame to a desired location and locking in position so as to set the X coordinate;

sliding said side mounted target assembly along said target frame to a desired location and locking said side target assembly in position providing coordinate Y; and sliding said top target assembly along said target frame to a desired location and locking in position for providing a coordinate Z.

23. The method of targeting according to claim 21 wherein said setting of an angle of lateral entry comprises the steps of:

sliding said interface along said base system frame until side stirrup aligns with a desired angle wherein said slide interface frame is locked in position; and adjusting a desired angle of the arch rotator with arch frame to match angle side stirrup and lock in position.

24. The method of targeting according to claim 21 wherein said setting of an angle of longitudinal entry comprises the steps of:

sliding said arch frame along said interface frame until said top stirrup aligns with a desired angle wherein said arch frame is locked in position; and sliding said delivery system along said arch assembly to match angle of said top stirrup wherein said delivery system is locked into position.

\* \* \* \* \*

UNITED STATES PATENT AND TRADEMARK OFFICE
CERTIFICATE OF CORRECTION

Page 1 of 1

PATENT NO.   : 5,665,095
DATED        : September 9, 1997
INVENTOR(S)  : Robert E. Jacobson It is certified that error appears in the above-identified patent and that said Letters Patent is hereby corrected as shown below:

Title page,
Below Item [19], "United States Patent", "Jacobson" should read -- Jacobson et al --;
Item [75] Inventors: -- Brian Mirson -- should be added as the second inventor.

Signed and Sealed this

First Day of January, 2002

Attest:

Attesting Officer

JAMES E. ROGAN
Director of the United States Patent and Trademark Office